United States Patent [19]

Chu

[11] 4,120,910
[45] Oct. 17, 1978

[54] AROMATIZATION OF ETHANE

[75] Inventor: Pochen Chu, West Deptford, N.J.

[73] Assignee: Mobil Oil Corporation, New York, N.Y.

[21] Appl. No.: 754,217

[22] Filed: Dec. 27, 1976

[51] Int. Cl.$^2$ .................... C07C 15/02; C01B 29/28; C01G 9/04
[52] U.S. Cl. ................................. 260/673; 208/120; 423/328
[58] Field of Search ............... 260/673, 683.3; 208/67, 208/71, 120

[56] References Cited

U.S. PATENT DOCUMENTS

| 3,760,024 | 9/1973 | Cattanach | 260/673 |
| 3,843,741 | 10/1974 | Yan | 260/673.5 |
| 3,845,150 | 10/1974 | Yan et al. | 260/673.5 |
| 3,928,483 | 12/1975 | Chang et al. | 260/668 R |

*Primary Examiner*—Delbert E. Gantz
*Assistant Examiner*—G. E. Schmitkons
*Attorney, Agent, or Firm*—Charles A. Huggett; Raymond W. Barclay; Howard M. Flournoy

[57] ABSTRACT

A catalytic process is provided for converting gaseous paraffinic feedstocks containing ethane to liquid aromatics by contacting said gaseous feeds, in the absence of added air or oxygen, under conversion conditions, with a crystalline aluminosilicate zeolite catalyst having incorporated therein a minor amount of a metal selected from Groups VIII, IIB and IB of the Periodic Table and mixtures thereof thereby converting ethane in said feed to aromatics and recovering said aromatics as liquids.

8 Claims, No Drawings

AROMATIZATION OF ETHANE

BACKGROUND OF THE INVENTION

1. Field of the Invention

This invention relates to a process for the conversion of a gaseous paraffinic feed containing ethane to liquid aromatics in the presence of a crystalline aluminosilicate zeolite-containing catalyst.

2. Description of the Prior Art

It has long been known to contact various hydrocarbon fractions and/or feeds with acidic catalysts and in particular, solid siliceous acidic catalysts—including crystalline aluminosilicate zeolites—for a wide variety of reactions including cracking, isomerization, hydrocracking, etc. Representative United States Patents disclosing such contacting with crystalline aluminosilicates are U.S. Pat. Nos. 3,140,251; 3,760,024; 3,775,501; 3,813,330; and 3,953,366.

Contacting paraffinic feedstocks with crystalline aluminosilicate zeolites is also known in the art, by far the primary reason for contacting paraffinic materials with zeolites has been for the purpose of cracking them, i.e., converting them to lower molecular weight products. Typical applications would be the use of crystalline aluminosilicate zeolites for carrying out dewaxing reactions, i.e., the cracking of paraffins to the low molecular weight materials.

The instant application is not concerned with hydrocarbon conversion in general, but rather, is concerned with the conversion of gaseous hydrocarbon feeds consisting essentially of paraffins, e.g., ethane to liquid aromatic compounds. Accordingly, the instant application in its most particular embodiment is concerned with the preparation of liquid aromatic compounds from ethane, i.e., the aromatization of ethane in commercially significant amounts. Up to now means to utilize ethane and other higher paraffins in for example associated gas or blow-by gas and other natural gases have mainly been confined to (1) separation and compression, e.g., methane is separated and the remaining paraffins including ethane are used as fuels or as liquifiable petroleum gas, (2) cracking and reforming, i.e. converting the gaseous feeds to ethylene and other related products.

The prior art contains many "disclosures" for aromatizing ethane but to applicant's knowledge there are none wherein significant or even appreciable amounts of ethane are converted to liquid aromatic compounds since ethane is relatively stable, inert and difficult to convert to aromatics. However, the instant process does convert appreciable amounts of ethane into aromatic compounds under less severe conditions than heretofore known to the art for most hydrocarbon conversion processes.

This application, as stated hereinabove is more particularly concerned with a process for producing aromatic compounds which comprises contacting, in the absence of added air or oxygen under conversion conditions, a gaseous, paraffinic feed containing a high percentage of ethane with a ZSM-5 type crystalline aluminosilicate zeolite catalyst having incorporated therein a minor amount of a metal or metal oxide wherein said metal is selected from the group consisting of a Group VIII, IIB or IB metal and mixtures thereof whereby ethane present in said gaseous feed is converted to aromatic compounds and recovering said aromatic compounds as liquids.

DESCRIPTION OF SPECIFIC EMBODIMENTS

The zeolite catalysts herein described are members of a novel class of zeolites exhibiting some unusual properties; they induce conversion of aliphatic hydrocarbons to aromatic hydrocarbons in commercially desirable yields and are also generally highly effective in conversion reactions involving aromatic hydrocarbons. Although they usually have low alumina contents, i.e., high silica to alumina ratios, they are very active even when the silica to alumina ratio exceeds 30. This activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments, the zeolites of this class exhibit very low coke forming capability which is conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms being bonded to the silicon or aluminum atoms at the centers of the tetrahedra. Briefly, the preferred type catalysts useful in this inventive process have a silica to alumina ratio of at least about 12 and a structure providing constrained access to the crystalline free space.

The silica to alumina ratio referred to can be determined by conventional analysis. This ratio is meant to represent, as closely as possible, the ratio in the rigid anionic framework of the zeolite crystal and to exclude aluminum in the binder or in cationic or other form within the channels.

The type zeolites useful in this invention freely sorb normal hexane and as mentioned above have a pore dimension greater than about 5 Angstroms. In addition, the structure should provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions desired, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatrography, to determine the fraction remaining unchanged for each of the two hydrocarbons.

The "constraint index" is calculated as follows:

$$\text{Constraint index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 which describes and claims ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in pending U.S. application Ser. No. 560,412, filed Mar. 20, 1975 (now U.S. Pat. No. 4,046,859). This zeolite can be indentified, in terms of mole ratios of oxides and in the anhydrous state, as follows:

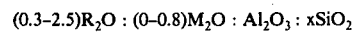
$$(0.3-2.5)R_2O : (0-0.8)M_2O : Al_2O_3 : xSiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of moles ratios of oxides and in the anhydrous state, as follows:

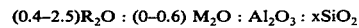
$$(0.4-2.5)R_2O : (0-0.6) M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and $x$ is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33Å.

TABLE I

| d (Å) | | | $I/I_o$ |
|---|---|---|---|
| 9.8 | ± | 0.20 | Strong |
| 9.1 | ± | 0.19 | Medium |
| 8.0 | ± | 0.16 | Weak |
| 7.1 | ± | 0.14 | Medium |
| 6.7 | ± | 0.14 | Medium |
| 6.0 | ± | 0.12 | Weak |
| 4.37 | ± | 0.09 | Weak |
| 4.23 | ± | 0.09 | Weak |
| 4.01 | ± | 0.08 | Very Strong |
| 3.81 | ± | 0.08 | Very Strong |
| 3.69 | ± | 0.07 | Medium |
| 3.57 | ± | 0.07 | Very Strong |
| 3.51 | ± | 0.07 | Very Strong |
| 3.34 | ± | 0.07 | Medium |
| 3.17 | ± | 0.06 | Strong |
| 3.08 | ± | 0.06 | Medium |
| 3.00 | ± | 0.06 | Weak |
| 2.92 | ± | 0.06 | Medium |
| 2.73 | ± | 0.06 | Weak |
| 2.66 | ± | 0.05 | Weak |
| 2.60 | ± | 0.05 | Weak |
| 2.49 | ± | 0.05 | Weak |

A further characteristic of ZSM-38 is its sorptive-capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2- methylpentane for ZSM-38 (after calcination at 600° C.) is less than 10, whereas that ratio for the natural ferrierite is substantially greater than 10, for example, as high as 34 or higher.

Zeolite, ZSM-38 can be suitable prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in pending U.S. application Ser. No. 528,061 (now U.S. Pat. No. 4,016,245), filed Nov. 29, 1974. This zeolite can be identified, in terms of mole ratios of oxides and in the anhydrous state, as follows:

$$(0.3-2.5)R_2O : (0-0.8)M_2O : Al_2O_3 : xSiO_2$$

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0.0.6)M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Å. Close examination of some individual samples of ZSM-35 may show a very weak line at 11.3–11.5Å. This very weak line, however, is determined not to be a significant line for ZSM-35.

TABLE II

| d (Å) | I/Io |
|---|---|
| 9.6 − 0.20 | Very Strong-Very Very Strong |
| 7.10− 0.15 | Medium |
| 6.98− 0.14 | Medium |
| 6.64± 0.14 | Medium |
| 5.78± 0.12 | Weak |
| 5.68± 0.12 | Weak |
| 4.97± 0.10 | Weak |
| 4.58± 0.09 | Weak |
| 3.99± 0.08 | Strong |
| 3.94± 0.08 | Medium Strong |
| 3.85± 0.08 | Medium |
| 3.78± 0.08 | Strong |
| 3.74± 0.08 | Weak |
| 3.66± 0.07 | Medium |
| 3.54± 0.07 | Very Strong |
| 3.48± 0.07 | Very Strong |
| 3.39± 0.07 | Weak |
| 3.32± 0.07 | Weak Medium |
| 3.14± 0.06 | Weak Medium |
| 2.90± 0.06 | Weak |
| 2.85± 0.06 | Weak |
| 2.71± 0.05 | Weak |
| 2.65± 0.05 | Weak |
| 2.62± 0.05 | Weak |
| 2.58± 0.05 | Weak |
| 2.54± 0.05 | Weak |
| 2.48± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts heretofore described are used in an acidic or hydrogen form or they may be base exchanged or impregnated to contain ammonium or a metal cation complement. Accordingly, the zeolite catalyst especially useful in this invention are the ZSM-5 type which of course includes ZSM-5, ZSM-11, ZSM-12, ZSM-38, ZSM-35 and other similarly behaving zeolites with ZSM-5 a preferred embodiment. It is desirable to calcine the catalyst after base exchange. The metal cations that may be present include any of the cations of the metals of Groups IB, IIB and VIII of the Periodic Table and mixtures thereof.

In a preferred aspect of this invention, the catalysts hereof are selected from those also having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erinonite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 50 percent by weight of the original alkali metal contained therein usually 0.5 wt. % or less may be used. Thus, as stated hereinabove the original alkali metal of the zeolite may be replaced by ion exchange with other suitable ions of Groups IB, IIB and VIII of the Periodic Table including, by way of example, zinc, copper or platinum groups metals and combinations thereof. Especially preferred is a zinc-copper mixture. The amount of metal so utilized can vary between wide limits, depending, interalia, or intended reaction conditions, etc. However, catalysts of the invention usually contain from about 0.01 to about 30 weight percent based on the weight of the total catalyst. Preferably from about 0.5 to about 10 weight percent metal is present in the catalyst.

One embodiment of this invention resides in the use of a porous matrix together with the zeolites previously described. The zeolites can be combined, dispersed or otherwise intimately admixed with a porous matrix in such proportions that the resulting product contains from 1% to about 95% by weight, and preferably from 10% to about 70% by weight of the zeolite in the final composite.

The term "porous matrix" includes inorganic compositions with which the aluminosilicates can be combined, dispersed or otherwise intimately admixed wherein the matrix may be active or inactive. It is to be understood that the porosity of the compositions employed as a matrix can either be inherent in the particular material or it can be introduced by mechanical or chemical means. Representative matrices which can be employed include metals and alloys thereof, sintered metals and sintered glass, asbestos, silicon carbide aggregates, pumice, firebrick, diatomaceous earths, alumina and inorganic oxides. Inorganic compositions especially those of a siliceous nature are preferred. Of these matrices, inorganic oxides such as clay, chemically treated clay, silica, alumina, and silica-alumina are highly advantageous.

The ZSM-5 can be conveniently prepared in accordance with U.S. Pat. No. 3,702,886. This patent as previously indicated and U.S. No. 3,709,979 and the aforementioned 3,775,501 are incorporated herein by reference for all they disclose concerning the synthesis and chemical and physical properties of ZSM-5 type zeolites.

The hydrogen or ammonium forms of ZSM-5 are also advantageously used in this invention. The metal containing catalysts of the invention can be prepared by impregnation or ion-exchange techniques well known to the art.

The gaseous feedstocks useful in the present process may be paraffinic feedstocks, or prepared mixtures, i.e., mixtures of ethane with other paraffins for example $C_3$-$C_8$. Particularly suitable are gas feeds which are primarily ethane, such as associated gas, gaseous cracker feeds, and blow-by gases.

The following examples are merely illustrative and are not to be construed as limiting the scope of the invention.

EXAMPLE 1

$NH_4ZSM-5$ catalyst was prepared as follows:

1. Synthesis of Zeolite

A sodium silicate solution was prepared by mixing 90.9 lb of silicate, a commercial sodium silicate, 20 g. of a commercial dispersant and 52.6 lb of water. An acid alum solution was prepared by mixing 2850 g. of $Al_2(SO_4)_3 \cdot 18H_2O$, 3440 g of $H_2SO_4$, 4890 g. of NaCl and 54 lb of water. The above two solutions were nozzle mixed together to form into gel in a 30 gallon autoclave. Additional 2840 g of NaCl was added and mixed into the gel. On top of the gel, 2780 g of tri-n-propylamine, 2390 g of n-propylbromide and 4590 g. of methyl ethyl ketone were added. The crystallization was carried out in three stages: 2 hours of pre-reaction at 210° F. without agitation, about 60 hours at 228° F. with 250 rpm agitation, and about 5.3 hours at 325° F. with 250 rpm agitation. The crystallized product was 100% ZSM-5 as measured by x-ray diffraction. The washed and dried product was analyzed and was found to be by wt 95% $SiO_2$, 3.99% $Al_2O_3$, 0.9% Na, 0.4% N, 7.58% C. and 90.9% ash.

2. Preparation of Catalyst

The $NH_4$ form was prepared by calcining the above mentioned synthesized, washed and dried product at 1000° F. for 3 hours in nitrogen atmosphere to remove carbonaceous material. The calcined product was then ion-exchanged with 1 N ammonium nitrate solution at ambient temperature for 4 hours. Two 4-hour exchanges are generally required to bring the residual Na content in the catalyst to less than 0.02% by weight.

EXAMPLES 2-5

A Cu—Zn/HZSM-5 was prepared from the $NH_4ZSM-5$ in Example 1 above by ion exchange with 0.1 N $Cu(NO_3)_2$ solution twice at 180° F. for 1 hour each, using 5 ml of solution per one gram of catalyst per exchange. The catalyst is ion exchanged one more time with 0.1 N $Zn(NO_3)_2$ solution at similar conditions. The washed and dried catalyst was slugged and sized to 14/20 mesh followed by final air calcination at 1000° F. for 3 hours. The catalyst was found to contain 0.25% Cu and 1% Zn by weight.

EXAMPLES 6-7

An $NH_4ZSM-5$ sample was prepared in accordance with Ex. 1 having a $SiO_2/Al_2O_3$ mol ratio of 70. The sample then was combined with an $Al_2O_3$ binder in the ratio of 65:35. The mixture was extruded thru a 1/16 inch die plate with an auger extruder. The Pt/HZSM-5 sample was prepared by impregnating the extrudates with calculated amount of $H_2PtCl_6$ solution to give 0.1 wt% of Pt in the final product. The resultant catalyst was activated at 1000° F. in air for 3 hours before test.

EXAMPLE 8

The Pt/HZSM-5 catalyst sample was prepared in a manner similar to Examples 6-7, except that the resultant catalyst contained 0.4% wt Pt.

EXAMPLE 9

An HZSM-5 extrudate was prepared by the procedure in Examples 6-7 with the exception of the impregnating step.

EXAMPLE 10

The Cu-HZSM-5 sample was prepared in a manner similar to those in Examples 2-5, except that this sample was ion-exchanged with 0.1 N $Cu(NO_3)_2$ solution only to give about 2.5 wt% of Cu.

EXAMPLE 11

The Zn-HZSM-5 sample was prepared in a manner similar to those in Examples 2-5 except that this sample was ion-exchanged with 0.1N $Zn(NO_3)_2$ solution only to give about 2.1 wt.% of Zn. The resultant catalyst was steamed at 1200° F. for 1.5 hours in 100% steam.

EXAMPLE 12-13

The catalyst of these examples are the same catalysts as those in Examples 2-5.

The above described catalysts, i.e., Examples 1-13 were then utilized in the process of this invention wherein liquid $C_6+$ aromatics were produced under varied operating conditions with catalysts having varied metal percentages from gaseous feeds containing ethane. The charge stock for Examples 2-11 was pure ethane, however, for Examples 12-13 it was changed from pure ethane to $CO_2$-$C_2H_6$ mixtures to demonstrate the effectiveness of these catalysts in the presence of other gaseous diluents. Table 1 summarizes characteristics of the catalysts (1) prepared in accordance with their designated Example number and (2) used in accordance with the hereinembodied aromatization process to obtain the data of Table 2. The data contained therein clearly demonstrate the utility of the disclosed process wherein the difficult to convert ethane is aromatized in the absence of added air or oxygen to liquid products in commercially attractive yields. Example 9 illustrates that when no metal was added to a catalyst otherwise in accordance with this invention little or no aromatization occurred. Also, the data of Table 2 demonstrates the superiority of the preferred Zn/Cu catalysts of the embodied invention.

It is understood that this application is not limited to the specific embodiments disclosed but that variations may be readily resorted to as will be readily understood by one of ordinary skill in the art.

TABLE 1

Catalyst:

TABLE 1-continued

| Example No. | 2-5 | 6-7 | 8 | 9 |
|---|---|---|---|---|
| | 0.1N Solutions At 180° F | | | |
| Ion exchanged Composition: | Cu(NO₃)₂/Zn(NO₃)₂ | H₂PtCl₆ | H₂PtCl₆ | — |
| SiO₂/Al₂O₃(mol/mol) | 40 | 70 | 70 | 70 |
| Binder (wt. %) | 0 | 35% Al₂O₃ | 35% Al₂O₃ | 35% Al₂O₃ |
| Metal (wt. %) | 0.25%Cu;1%Zn | 0.1% Pt | 0.4% Pt | 0% |

All of the Examples were dried at about 230° F and recalcined for approximately 3 hours at about 1000° F.

Catalyst:

| Example No. | 10 | 11 | 12-13 |
|---|---|---|---|
| | 0.1N Solutions at 180° F | | |
| Ion Exchanged Composition: | CuCl₂/Cu(NO₃)₂ | Zn(NO₃)₂ | Cu(NO₃)₂/ Zn(NO₃)₂ |
| SiO₂/Al₂O₃(mol/mol) | 40 | 40 | 40 |
| Binder (wt. %) | 0 | 0 | 0 |
| Metal (wt. %) | 2.5% Cu | 2.1% Zn | 0.25% Cu, 1% Zn |

TABLE 2

| Catalyst EXAMPLE No. | 2 | 3 | 4 | 5 | 6 | 7 |
|---|---|---|---|---|---|---|
| Charge Stock[1] | | | | | | |
| Operating Conditions[2] | | | | | | |
| Weight of Cat., g. | 1.0 | 1.0 | 1.0 | | 1.54 | |
| Charge Rate, ml/min. | 27 | 9 | 13.5 | | 13.5 | |
| WHSV (on zeolite) hr⁻¹ | 2.0 | 0.67 | 1 | | 1 | |
| Time on Stream, min. | 5 | 10 | 5 | 40 | 5 | 40 |
| Test Results: | | | | | | |
| Conv. Wt. % | 19.24 | 31.75 | 31.28 | 34.53 | 15.85 | 10.34 |
| Total Arom. Wt. % | 14.26 | 19.05 | 19.09 | 21.53 | 7.63 | 6.06 |
| Product Dist., Wt. % | | | | | | |
| C₁ | 3.48 | 11.63 | 11.26 | 12.07 | 5.91 | 2.32 |
| C₂ | | | | | | |
| C₂= | 1.31 | 1.02 | 0.93 | 0.92 | 1.97 | 1.63 |
| C₃-C₅ | 0.20 | 0.04 | — | TRACE | 0.34 | 0.33 |
| Total Non Arom., Wt. % | .75 | 0.94 | 12.19 | 12.99 | 8.22 | 4.28 |
| Benzene | 4.62 | 5.74 | 5.91 | 6.29 | 3.15 | 2.66 |
| Toluene | 3.90 | 3.88 | 3.48 | 4.18 | 2.91 | 2.35 |
| C₈ Arom. | 0.95 | 0.78 | 0.44 | 0.69 | 0.89 | 0.53 |
| C₉+ Arom. | 4.79 | 8.65 | 9.26 | 10.37 | 0.68 | 0.52 |
| Total Arom., Wt. % | 14.26 | 19.05 | 21.53 | 7.63 | 6.06 | |

| Catalyst EXAMPLE NO. | 8 | 9 | 10 | 11 | 12 | 13 |
|---|---|---|---|---|---|---|
| Charge Stock[1] | | | | ETHANE | 50%CO₂ + 50% | ETHANE |
| Operating Condition[2] | | | | | | |
| Temperature °F | | | | 1100 | 1000 | 1100 |
| Weight of Cat., g. | 1.54 | 1.54 | 1.0 | 1.0 | 1.0 | 1.0 |
| Charge Rate, ml/min. | 13.5 | 13.5 | 13.5 | 13.5 | 27 | 27 |
| WHSV (on zeolite)hr⁻¹ | 1.0 | 1 | 1 | 1.0 | 1(C₂H₆) | 1(C₁(CH₆)) |
| Time on Stream, min. | 5 | 5 | 5 | 5 | 5 | 10 |
| Test Results: | | | | | | |
| Conv. Wt. % | 31.97 | 1.31 | 12.84 | 10.97 | 6.50 | 19.88 |
| Total Arom. Wt. % | 10.59 | 0.32 | 10.34 | 8.06 | 4.23 | 12.24 |
| Product Dist., Wt. % | | | | | | |
| C₁ | 19.57 | 0.51 | 1.85 | 1.40 | 1.60 | 6.60 |
| C₂ | — | — | — | — | — | — |
| C₂= | 1.64 | 0.49 | 0.64 | 1.19 | 0.60 | 0.84 |
| C₃-C₅ | 0.21 | TRACE | TRACE | 0.31 | 0.07 | 0.12 |
| Total Non Arom., Wt. % | 21.6 | 1.00 | 2.49 | 2.90 | 2.27 | 7.64 |
| Benzene | 4.87 | 0.11 | 3.34 | 3.32 | 1.67 | 4.87 |
| Toluene | 3.68 | 0.21 | 1.03 | 3.00 | 1.52 | 3.30 |
| C₈ Arom. | 0.78 | — | — | 0.60 | 0.29 | 0.46 |
| C₉+ Arom. | 1.26 | — | 5.97 | 1.14 | 0.75 | 3.70 |
| Total Arom., Wt. % | 10.59 | 0.32 | 10.34 | 8.06 | 4.23 | 12.24 |

1. Charge Stock ethane all cases except for Examples 12 and 13 where it was 50% CO₂ and 50% ethane.
2. Operating conditions all cases, atmospheric pressure at 1100° F, except for Example 12 where it was at 1000° F.

What is claimed is:

1. A process for producing aromatic compounds which comprises contacting, in the absence of added air or oxygen under conversion conditions, a gaseous paraffinic hydrocarbon feed containing ethane, with a catalyst comprising a crystalline aluminosilicate zeolite characterized by a constraint index within the approximate range of 1 to 12 and a silica to alumina ratio of at least 12, said catalyst having incorporated therein from about 0.01 to 30 weight percent based on the total weight of the catalyst of a metal or metal oxide wherein said metal is selected from the group consisting of Group VIII, IIB and IB metals and mixtures thereof whereby ethane present in said gaseous feed is converted to aromatic compounds and recovering said aromatic compounds as liquids.

2. The process of claim 1 wherein the metal is selected from the group consisting of copper, zinc, ruthenium, rhenium, rhodium, palladium, platinum, iridium, osmium and mixtures thereof.

3. The process of claim 2 wherein the metal is copper or zinc or a mixture thereof.

4. The process of claim 1 wherein the catalyst contains said metal or metal oxide in an amount from about 0.5 to about 10 weight percent based on the total weight of the catalyst.

5. The process of claim 1 wherein the conversion conditions include a temperature of from about 500° to about 1300° F., a pressure of from about atmospheric to about 100 atmospheres and a WHSV of from about 0.5 to about 100.

6. The process of claim 1 wherein said crystalline aluminosilicate zeolite is selected from the group consisting of ZSM-5, ZSM-11, ZSM-12, ZSM-35, and ZSM-38.

7. The process of claim 6 wherein said zeolite is an acid form.

8. The process of claim 7 wherein said zeolite is a HZSM-5 zeolite.

* * * * *